United States Patent [19]

Pyke et al.

[11] Patent Number: 4,730,479
[45] Date of Patent: Mar. 15, 1988

[54] TEMPERATURE AND HUMIDITY COMPENSATION FOR GAS DETECTION APPARATUS

[75] Inventors: Stephen C. Pyke, Willowick; Donald L. Boos, Cleveland; Milton L. Brouwer, Warrensville Heights, all of Ohio

[73] Assignee: The Standard Oil Company, Cleveland, Ohio

[21] Appl. No.: 877,631

[22] Filed: Jun. 23, 1986

[51] Int. Cl.[4] ............................................ G01N 27/04
[52] U.S. Cl. ............................................ 73/23; 73/27 R
[58] Field of Search ............... 73/23, 27 R, 19 US; 340/632, 634; 422/98; 357/25; 338/34, 14

[56] References Cited

U.S. PATENT DOCUMENTS

| | | | |
|---|---|---|---|
| 3,831,432 | 8/1974 | Cox | 73/23 |
| 4,064,498 | 12/1977 | Burr et al. | 340/632 |
| 4,112,356 | 9/1978 | Toy | 73/27 R |
| 4,147,513 | 4/1979 | Bienkowski et al. | 73/23 |
| 4,151,503 | 4/1979 | Cermak et al. | 73/27 R |
| 4,233,033 | 11/1980 | Eifler et al. | 73/27 R |
| 4,344,317 | 8/1982 | Hottori et al. | 73/23 |
| 4,443,791 | 4/1984 | Risgin et al. | 422/98 |
| 4,656,455 | 4/1987 | Tanino et al. | 73/27 R |

FOREIGN PATENT DOCUMENTS 2075195  11/1981  United Kingdom ................. 73/23

Primary Examiner—Stewart J. Levy
Assistant Examiner—Hezron E. Williams
Attorney, Agent, or Firm—Jeffrey A. Wyand; Joseph G. Curatolo; Larry W. Evans

[57] ABSTRACT

The use of multiple field effect transistors, wherein only one transistor is sensitive to the presence of a particular element, is disclosed whereby similar responses to temperature and/or humidity fluctuations may be subtracted yielding a response to a particular element that is relatively insensitive to temperature and/or humidity variations.

14 Claims, 1 Drawing Figure

TEMPERATURE AND HUMIDITY COMPENSATION FOR GAS DETECTION APPARATUS

FIELD OF THE INVENTION

The present invention relates to a method of and devices for continuously monitoring and detecting concentrations of specific gases, and for warning when such concentrations exceed predetermined threshold concentrations. More specifically, the present invention relates to an improved apparatus for the detection of concentrations of specific gaseous compounds, which apparatus is not sensitive to temperature and/or humidity fluctuations.

BACKGROUND OF THE INVENTION

Gas monitors and gas detection devices are well-known, having been developed as analytical tools and for use in monitoring commercial operations where it is necessary to detect the presence of a particular gas. Gas detection devices are now in increasing demand to monitor the quality of air in the workplace, especially to detect the presence of high levels of a toxic or combustible gas. Due to the varied properties of gases to be monitored and the widespread conditions under which such devices are needed, many devices have been developed for monitoring and detecting gases, each which suits the particular circumstances and environment where the device is to be used.

These devices operate on diverse technologies such as optical, chemical, gas chromatographic, electrochemical, and catalytic detection. Optical devices rely on detection of the infrared absorption spectra of the gas to be monitored. Such systems are expensive and not portable. Continuous monitoring and immediate feed back is not feasible with such a device. Devices which rely on chemical reactions, such as calorometric systems, are slow, non-continuous and costly. A device which utilizes gas chromatography to detect the presence of a particular gas also has inherently slow response time and cannot provide a continuous monitoring of the environment to detect the indicated gas. Electrochemical gas detection generally occurs in a cell wherein an oxidation-reduction reaction occurs with the gas to be detected dissolved in an electrolyte. This type of system is generally not highly selective for the particular gas to be detected. Devices which utilize catalytic sensors generally rely on a thermotype sensor which measures the temperature change of the catalytic material or a semiconductor catalytic sensor. Well-known semiconductor type sensors used in alarm devices and analyzers to date include zirconium oxide, titanium oxide, indium oxide, tin oxide, tungsten oxide, platinum and palladium doped metal oxides, and mixtures thereof. These semiconductor materials generally monitor the impedance changes in the oxide when a catalytic reaction takes place. The semiconductor material is generally heated to provide a controlled reaction environment. Hooker recognized that semiconductor catalytic sensors are sensitive to humidity and provided a moisturizing ring to surround the sensor in his U.S. Pat. No. 3,933,433 entitled, "Method and Apparatus for Gas Detection".

Recently, silicon based devices have been reported which have sensitivities to particular gases. Lundstrom et al. reported in *Applied Physics Letters*, Vol. 26, No. 2, Jan. 15, 1975, a hydrogen-sensitive MOS field effect transistor which comprised an MOS field effect transistor having a thin palladium film as the gate electrode. Such sensors however, have not been widely commercialized to date.

A major drawback to the commercialized technologies for detecting gas concentrations is the bulk size and power requirements of the detection device. Although permanently mounted fixed monitors may be placed in high risk areas, there is also a great demand to provide portable, light-weight and reliable devices that can continuously monitor and detect significant concentrations of desired gases. Such a monitor may be worn by an individual and continuously monitor the atmospheres to which the individual is exposed as the individual moves throughout the workplace.

Co-pending patent application, U.S. Ser. No. 811,548, entitled "Method and Device for Detection of Changes in Gas Concentration", discloses a light weight, low-power apparatus for continuously monitoring the concentration of at least one selected gas and means for signaling when the gas concentration suddenly increases. The apparatus described therein comprises at least one semiconductor sensor that is sensitive to at least one selected gas and electronic circuitry for monitoring the current changes produced in the semiconductor device. The electronic circuitry produces a voltage change in response to the current output from the semiconductor sensor which is monitored through integrating operational amplifiers. The amplifiers have differing time constants so that voltage changes produce unequal voltage responses. When the voltage responses deviate in a manner indicating sudden gas concentration changes an alarm is activated. While this apparatus is a significant improvement to the field of personal safety alarms, it, like previous gas detection devices, may not respond similarly under various conditions of temperature and humidity. This is a drawback to a portable gas detection device relied upon by an individual who may travel through localized areas having widely differing temperature and humidity levels.

It would be a significant contribution to the field of portable gas detection devices to provide a gas detection and alarm device that is miniature, light-weight, low-power and relatively insensitive to at least one of temperature and humidity fluctuations.

Thus, one object of the present invention is to provide a gas detection and alarm device that is not affected by variations in at least one of temperature and humidity.

It is another object of the present invention to provide a method for the detection of changes in gas concentrations, that is relatively insensitive to at least one of temperature and humidity fluctuations.

These and other objects of the present invention will become obvious to one skilled in the art from the below description of the invention and the appended claims.

SUMMARY OF THE INVENTION

The present invention relates to an apparatus for monitoring the concentration of at least one selected gas and means for signaling when the gas concentration exceeds a predetermined threshold, which apparatus comprises:

a first semiconductor sensor that is sensitive to at least one condition of temperature and humidity variation and to at least one selected gas;

at least a second semiconductor sensor that is sensitive to the same at least one condition of temperature and humidity variation and substantially insensitive to its chemical environment;

means for adjusting the at least one condition of temperature and humidity dependence of one semiconductor sensor so as to be substantially the same as the dependence of the other semiconductor sensor;

means for obtaining an adjusted first semiconductor response by subtracting the sensor response of the second semicondutor sensor from the sensor response of the first semiconductor sensor to eliminate the first semiconductor's response due to the at least one condition of temperature and humidity variation; and means for monitoring the adjusted first semiconductor response and for signaling when the gas concentration exceeds a predetermined threshold.

The present invention also relates to a method of monitoring changes in gas concentrations that is insensitive to at least one condition of temperature and humidity variation, which method includes the steps of:

providing a first semiconductor sensor that is sensitive to at least one condition of temperature and humidity variation and to at least one selected gas;

providing at least a second semiconductor sensor that is sensitive to the same at least one condition of temperature and humidity variation and substantially insensitive to its chemical environment;

adjusting the at least one condition of temperature and humidity dependence of one semiconductor sensor so as to be substantially the same as the dependence of the other semiconductor sensor;

subtracting the sensor response of the second semiconductor sensor from the sensor response of the first semiconductor sensor to eliminate the first semiconductor's response due to the at least one condition of temperature and humidity variation; and monitoring the adjusted first semiconductor response to detect changes in the concentration of the at least one selected gas.

DETAILED DESCRIPTION OF THE INVENTION

In accordance with the present invention there is provided an apparatus and method for monitoring the environment to detect the presence of at least one preselected gas, which apparatus and method is not significantly affected by temperature and humidity fluctuations.

The apparatus taught herein utilizes the chemical sensitivity characteristics of semiconductor sensors. Semiconductor sensors for use in the apparatus taught herein generally comprise materials such as silicon or germanium, and preferably are silicon-based sensors. These sensors most often are provided as field-effect transistors, such as the MOS field-effect transistor disclosed in "A Hydrogen-Sensitive MOS Field-Effect Transistor" reported by I. Lundstrom et al. in *Applied Physics Letters*, Vol. 26, No. 2, Jan. 15, 1975, and suspended gate field-effect transistors described in U.S. Pat. No. 4,441,741 entitled "Apparatus and Method for Measuring the Concentration of Components in Fluids" to Janata.

The gate electrode of the field-effect transistor sensors may comprise various materials of coatings which impart different chemical sensitivities to the field-effect transistor. As an example, the MOS field-effect transistor disclosed by Lundstrom above, utilizes a thin palladium film as the gate electrode and is sensitive to the concentration of hydrogen in the atmosphere around the device. Similarly, it is known that gold is sensitive to hydrogen sulfide; nickel and zirconium are sensitive to carbon monoxide; and platinum and tungsten are sensitive to hydrogen. By determining the sensitivity of an element or alloy to a given gas, a semiconductor sensor sensitive to that gas can be manufactured. In this way, semiconductor sensor devices able to detect hydrogen, hydrogen sulfide, methane, carbon monoxide, oxygen, alcohols, water vapor, various low molecular weight hydrocarbons and other gaseous compounds may be provided for use in the subject apparatus.

Chemical changes in the semiconductor sensor, as a result of detecting a desired gas, give rise to electrical current changes. The current output from the semiconductor sensor is then channeled through electronic circuitry to analyze such electrical changes. Preferably, electrical changes are analyzed by thick film circuitry for miniaturization and its associated components that inherently require only very low power. Such miniature devices are disclosed in co-pending U.S. patent application, Ser. No. 811,548, entitled "Method and Device for Detection of Changes in Gas Concentration". These devices provide continuous monitoring of the environment with very low power requirements. Thick film circuitry is preferred for use with the semiconductor sensors as the means for adjusting, substracting and monitoring the responses from the various semiconductor sensors.

The same semiconductor materials also undesirably produce changes in their electrical output as the temperature and humidity fluctuate in the environment surrounding the sensor. As taught herein, temperature and/or humidity variations may be compensated, and made substantially inconsequential, by the use of at least two semiconductor sensors disposed in parallel, wherein the first semiconductor sensor is sensitive to at least one selected gas in addition to its inherent sensitivity to the surrounding temperature and/or humidity and the second semiconductor sensor is sensitive to the surrounding temperature and/or humidity but insensitive to the chemical environment in which it is disposed.

A suspended gate field-effect transistor, (SGFET) may be used to detect the presence of a gas in the environment to which it is sensitive, and also be coupled with an MOS field-effect transistor that is not sensitive to the gas to be detected, but which does exhibit a sensitivity to temperature variations that can be related to the temperature drift observed in the SGFET device. In this way, the temperature effect on the SGFET may be determined and eliminated so as to maintain the SGFET as an accurate detector of gas, not affected by temperature fluctuations.

Similarly, a suspended gate field-effect transistor may be used to monitor the level of a particular gas and be associated with a second SGFET, not having a suspended gate of the same material, and so not sensitive to the same gas, but having a relatively similar sensor drift with humidity variations.

Combinations of such field-effect transistors can be envisioned within the purview of this disclosure that can provide individual and multiple gas monitoring/detection capacities that remain accurate over a wide range of temperatures, such as from about zero degrees C. to about 100 degrees C., and a wide range of humidities, such as from about ten percent to about 100 percent relative humidity.

The apparatus and method of detecting changes in gas concentrations not affected by temperature and/or humidity fluctuations which have been discussed herein will become more evident upon reading the following detailed description taken in conjunction with the drawing, wherein FIG. 1 is a circuit diagram showing one embodiment of the present invention.

DESCRIPTION OF THE DRAWINGS

Referring to this FIG. 1, there are shown two semiconductor field-effect transistors 1 and 2. One of the field-effect transistors designated by the numeral 1 is sensitive to chemical changes in its environment while the second, identified by the number 2, is relatively inert to chemical changes. As shown in block 10, field-effect transistor 1 may be a hydrogen sensitive such as SGFET device having a platinum suspended gate device having source 3, drain 4, and gate 5 electrodes.

The ungrounded terminal of a constant voltage source 6 is connected to drain electrode 4. Source electrode 3 is connected to ground through a resistor 8. The constant voltage from source 6 is dropped across source and drain electrodes 3, 4 and resistor 8. Changes in source to drain current alter the proportions of the constant voltage that are dropped across field-effect transistor 1 and resistor 8. The voltage across resistor 8 is applied to the negative sense terminal of an operational amplifier 9 by connecting source electrode 3 to that negative sense terminal.

Figure 1:
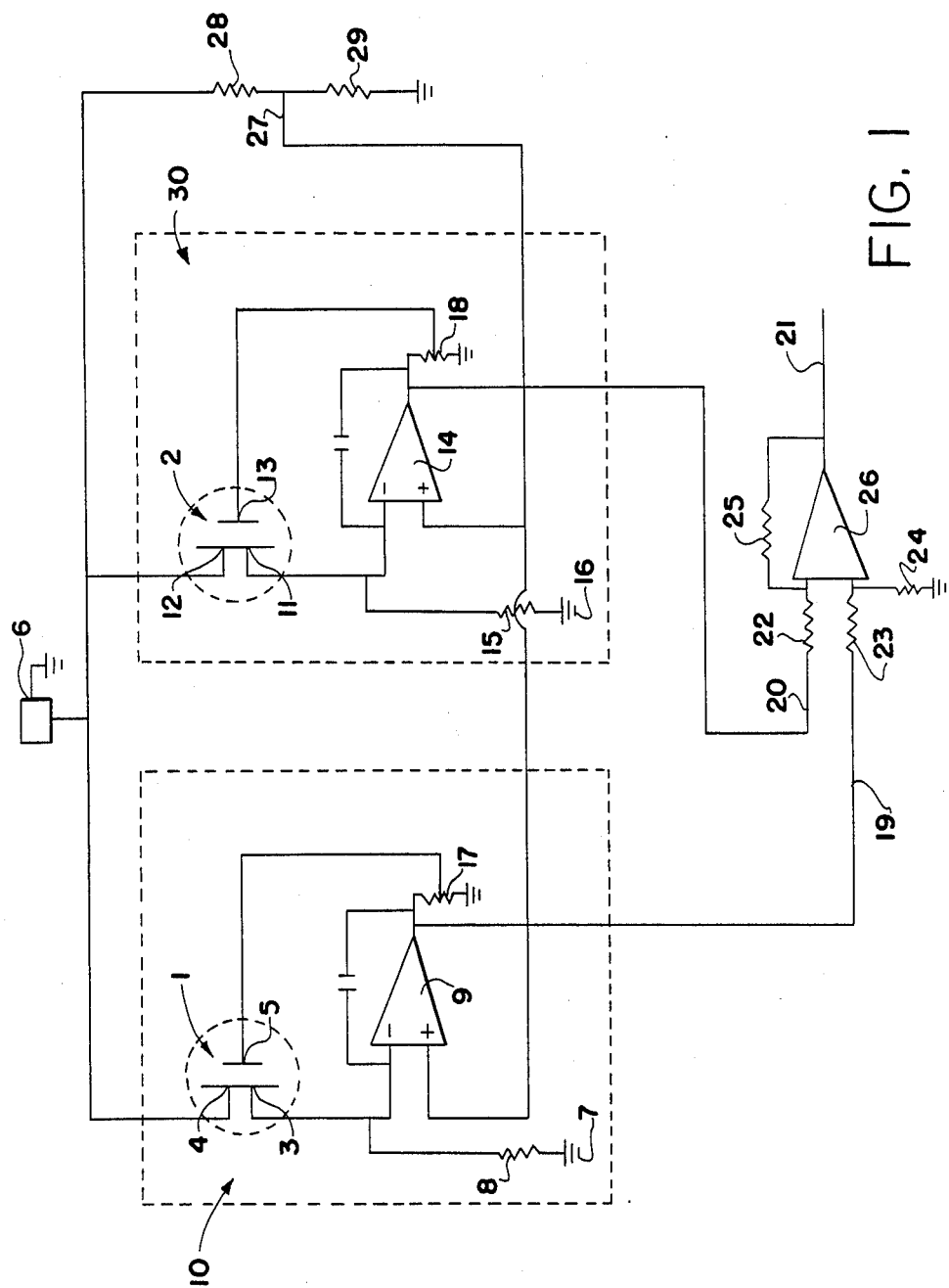

The ungrounded terminal of constant voltage source 6 is also connected to one end of a resistor 28. The opposed terminal of resistor 28 is connected at point 27 to a resistor 29, the opposite end of which is grounded. Series connected resistors 28 and 29 form a voltage divider providing a constant voltage at point 27 that is of a lower amplitude than that of voltage source 6. Point 27 is connected to the positive sense input terminal of operational amplifier 9 as a reference voltage. The output terminal of operational amplifier 9 is connected to ground through a potentiometer 17 having a variable position voltage tap terminal. The tap terminal is connected to gate electrode 5 of field-effect transistor 1. Operational amplifier 9 is conventional, supplying at its output terminal a signal having an amplitude that indicates the algebraic difference between the amplitudes of the signal applied at the positive and negative sense terminals. The gate electrode 5 is coated with a material that sensitizes the sensor 1 to the presence of at least one gas in the gap between the electrodes, such as the platinum-coated gate electrode 5 which is selectively sensitive to hydrogen.

In the steady state and the absence of the gas to which field-effect transistor 1 is responsive, a fixed current flows between drain and source electrodes 4 and 3 that is essentially equal to the voltage at point 27 divided by the resistance of resistor 8. That is, there is little voltage drop across the drain and source electrodes, the voltage on gate electrode 5 is essentially zero and the voltage across resistor 8 is essentially the same as that across resistor 29. When a gas to be monitored is detected in the gap, the sensitized gate electrode 5 becomes more positive altering the flow of current between the source and drain electrode and, thereby, the voltage drop across resistor 8. Operational amplifier 9 responds by generating an error signal that is applied to gate electrode 5, changing the current flow between the source and drain electrodes. This change drives the voltage across resistor 8 back towards the voltage present at point 27. When that voltage, i.e., the steady state, is reached, the output voltage of operational amplifier 9 provides an indication of the concentration of the gas that altered the voltage on gate 5. Fluctuations in temperature and humidity in the vicinity of the semiconductor sensor gap also cause the voltage on gate 5 between source 3 and drain 4 to change. This shift is corrected by the operational amplifier 9 in the same manner just described for gas detection. That is, a temperature and/or humidity change produces the same sort of voltage change in the circuit that is indicative of gas detection. This false gas detection is eliminated by the operation of the temperature compensation portion of the circuit shown in block 30.

There is shown in block 30 a field effect transistor 2 that is substantially insensitive to its chemical environment. The circuitry in block 30 is essentially the same as that shown in block 10 except that field-effect transistor 2 is not responsive to gases. This field-effect transistor 2 may be an MOS device having source 11, drain 12, and gate 13 electrodes. The drain electrode 12 is connected to the ungrounded terminal of constant voltage source 6. Source electrode 11 is connected to ground through a resistor 15 and is connected to the negative sense input terminal of an operational amplifier 14. The positive sense input terminal of operational amplifier 14 is connected to point 27. The output terminal of operational amplifier 14 is connected to gate electrode 13 of field-effect transistor 2. Field-effect transistor 2 is preferably an MOS type field-effect transistor that is unresponsive to the presence of gases, but does respond to temperature fluctuations in a manner similar to field-effect transistor 1.

The circuitry of block 30 responds just like that of block 10, except that it is responsive only to changes in temperature and/or humidity. When a temperature change causes a change in the current flow between sources 11 and drain 12, the output signal from operational amplifier 14 responds, changing the voltage on gate 13 until the original source-drain current flow is restored. The output signal from the operational amplifier 14 may be compared by additional means to the output signal from operational amplifier 9 to determine that portion of the output from amplifier 9 due to temperature effects and that portion due to hydrogen detection.

Additional circuitry is shown incorporated so as to provide the apparatus with the ability to calibrate each field-effect transistor's sensitivity to temperature, and further, to adjust one field-effect transistor's temperature relative to the other's so that the two sensitivities are linear. In the drawing, the current through variable resistors 17 and 18 can be adjusted so as to bring the signal in lines 19 and 20 into substantially similar temperature responses, following the formula $(V_{19})/T = (V_{20}/T)$ wherein $V_{19}$ is the voltage change in line 19, $V_{20}$ is the voltage change in line 20, and T is the temperature variation. These adjusted signals can be subtracted through amplifier 26 to yield a hydrogen response signal at point 21 that is substantially insensitive to temperature fluctuations. Other circuitry would be obvious to those skilled in the art to provide signal compensation for temperature and humidity variations.

It is to be understood that the foregoing drawing has been provided to enable those skilled in the art to evaluate the invention and that this drawing should not be construed as a limitation on the scope of this invention. Inasmuch as the semiconductor devices and their ancilliary electronic circuitry can be varied within the scope of the total Specification disclosure, neither the particular semiconductor devices nor the electrical configuration in which they are shown disposed shall be construed as limitations of the invention.

Whereas the above drawing incorporated a chemically sensitive suspended gate field-effect transistor and a chemically insensitive MOS transistor to negate temperature changes, other semiconductor designs as discussed earlier are available to compensate for humidity fluctuations. As an example, a field-effect transistor having a platinum suspended gate is sensitive to hydrogen while a similar field-effect transistor having a gold suspended gate is insensitive to hydrogen, but both devices show a similar sensitivity to changes in humidity. Thus a hydrogen gas detector that is substantially insensitive to temperature and humidity fluctuations may comprise a hydrogen sensitive SGFET having a platinum suspended gate, a hydrogen-insensitive MOS device to compensate for temperature and/or humidity fluctuations and a hydrogen insensitive SGFET having a gold suspended gate to compensate for humidity and/or temperature variations.

The device combinations taught herein provide novel gas detection devices that are substantially unaffected by changes in temperature and/or humidity, and so represent a substantial advancement to semiconductor gas detection devices having heretofore unattainable stability in environments of fluctuating temperature and humidity.

Thus it is believed that any of the variables disclosed herein can readily be determined and controlled without departing from the spirit of the invention herein disclosed and described. Moreover, the scope of the invention shall include all modifications and variations that fall within the scope of the attached claims.

We claim:

1. A compensated apparatus for monitoring the concentration of at least one selected gas comprising:
    a first three terminal field-effect transistor sensor that is responsive to at least one of changes in temperature and humidity and to at least one selected gas;
    at least a second field-effect transistor sensor that is responsive to the same at least one of changes in temperature and humidity that said first sensor is and is substantially unresponsive to said at least one selected gas;
    means for adjusting the response of at least one of said first and second sensors so that the responses of said sensors to said at least one of said changes in temperature and humidity are essentially the same; and
    means for subtracting the response of the second sensor from the response of the first sensor to compensate for the response of said first sensor to changes in the at least one of temperature and humidity.

2. The apparatus in accordance with claim 1 wherein said first sensor is a suspended gate field-effect transistor.

3. The apparatus in accordance with claim 1 wherein said first sensor is an MOS field-effect transistor.

4. The apparatus in accordance with claim 1 wherein said second sensor is a suspended gate field-effect transistor.

5. The apparatus in accordance with claim 1 wherein said second sensor is an MOS field-effect transistor.

6. The apparatus in accordance with claim 1 wherein said first and second sensors respectively generate a first electrical signal in response to said at least one gas and said changes in at least one of temperature and humidity and a second electrical signal in response to changes in at least one of temperature and humidity.

7. The apparatus in accordance with claim 6 wherein said means for subtracting comprises a differential amplifier having two input terminals and one of said first and second electrical signals is applied to each of said input terminals.

8. The apparatus in accordance with claim 1 wherein each field-effect transistor sensor includes a source electrode, a drain electrode and a gate electrode and comprising signal generating means having an output terminal and two input terminals of opposite senses for generating a signal at the output terminal indicating the magnitude of the difference between the signals applied to said input terminals, said output terminal being connected to the gate electrode of one of said sensors, a constant voltage source for generating a constant voltage, a first portion of said constant voltage being applied across said source and drain electrodes of said one of said sensors, the voltage difference between said constant voltage and said first portion being applied to one of said input terminals of said signal generating means, and a second portion of said constant voltage being applied to the other of said input terminals.

9. The apparatus in accordance with claim 8 wherein said means for adjusting includes a potentiometer having a variable position terminal, said potentiometer being connected from said output terminal to ground and wherein said variable position terminal is connected to said gate electrode.

10. A method of monitoring changes in gas concentration that is substantially insensitive to changes in at least one of temperature and humidity comprising:
    sensing the concentration of at least one selected gas with a first three terminal field-effect transistor sensor that is responsive to changes in at least one of temperature and humidity and to said at least one selected gas;
    sensing the change in said at least one condition with a second field-effect transistor sensor that has the same response to the same at least one of changes in temperature and humidity that said first sensor has and is substantially unresponsive to said at least one selected gas;
    adjusting the responses of at least one of said first and second sensors so that the responses of said sensors to said at least one of said changes in temperature and humidity are essentially the same;
    subtracting the response of said second sensor from the response of the first sensor to compensate for the response of the first sensor to changes in the at least one of temperature and humidity; and
    monitoring the compensated response of said first sensor to detect changes in the concentration of the at least one selected gas.

11. The method in accordance with claim 10 including sensing as said at least one selected gas one of the group consisting of hydrogen, hydrogen sulfide, methane, carbon monoxide, oxygen, alcohols, and water vapor.

12. The method in accordance with claim 10 including sensing said gas with a suspended gate field-effect transistor.

13. The method in accordance with claim 10 including sensing said changes in at least one of temperature and humidity with a suspended gate field-effect transistor.

14. The method in accordance with claim 10 including sensing said changes in at least one of temperature and humidity with an MOS field-effect transistor.

* * * * *